(12) United States Patent
Bryson et al.

(10) Patent No.: US 6,734,664 B2
(45) Date of Patent: May 11, 2004

(54) COMPLIANT LAMINAR EDDY CURRENT SENSITIVITY STANDARD

(75) Inventors: David A. Bryson, E. Hartford, CT (US); Chris Vargas, Rocky Hill, CT (US)

(73) Assignee: United Technologies Corporation, Hartford, CT (US)

( * ) Notice: Subject to any disclaimer, the term of this patent is extended or adjusted under 35 U.S.C. 154(b) by 112 days.

(21) Appl. No.: 09/917,979

(22) Filed: Jul. 30, 2001

(65) Prior Publication Data

US 2003/0020462 A1 Jan. 30, 2003

(51) Int. Cl.⁷ ............................................. G01R 35/00
(52) U.S. Cl. ........................................................ 324/202
(58) Field of Search ........................ 324/202; 156/245; 340/572.1, 572.3, 572.8

(56) References Cited

U.S. PATENT DOCUMENTS 3,582,772 A * 6/1971 Hammer .................. 324/202
6,121,880 A * 9/2000 Scott et al. ............... 340/572.5
6,235,385 B1 * 5/2001 Lee ........................... 428/344

FOREIGN PATENT DOCUMENTS

| EP | 0 969 267 | 1/2000 |
| WO | 9837564 | 8/1998 |

OTHER PUBLICATIONS

Patent Abstract of Japan, vol. 007, No. 253, Nov. 10, 1983 & JP 58 135954.
Patent Abstracts of Japan, vol. 1999, No. 05, May 31, 1999 & JP 11 050023.
Patent Abstracts of Japan, vol. 1998, No. 11, Sep. 30, 1998 & JP 10 165391.

* cited by examiner

Primary Examiner—Walter E. Snow
(74) Attorney, Agent, or Firm—Bachman & LaPointe, P.C.

(57) ABSTRACT

The present invention relates to a compliant laminar eddy current sensitivity standard which comprises a sheet of nonconductive, nonmagnetic material having at least one strand of highly conductive metallic material embedded in the sheet and an adhesive layer attached to a surface of the nonconductive, nonmagnetic material to allow the standard to be adhered to a surface of a part to be inspected. A method using the compliant laminar eddy current sensitivity standard is also described.

18 Claims, 2 Drawing Sheets

COMPLIANT LAMINAR EDDY CURRENT SENSITIVITY STANDARD

BACKGROUND OF THE INVENTION

The present invention relates to an eddy current sensitivity setting standard and a method for using the eddy current sensitivity setting standard.

In the past, an eddy current sensitivity standard was fabricated by machining an EDM slot into the critical inspection area of a section of a part to be inspected. The use of a section of the inspected component as the standard was critical because the typical eddy current probe responds to numerous benign electrical changes (electrical conductivity and permeability) induced by interaction with the metal surface under inspection other than those produced by a flaw such as a crack. Typically, the eddy current probe is sensitive to surface roughness, variations in conductivity/permeability within acceptable limits, geometric variations along the scan path, such as edges, radii, and/or slots, liftoff, and the like. All inspection surface parameters that affect the eddy current signal must be simulated in the standard to produce an accurate eddy current signature. If all the parameters affecting the eddy current response were not represented in the standard design, it would be impossible to separate the effects of the benign surface electric and geometric variations from a defect response.

As components being inspected are now extremely expensive, it has become impractical to consume good hardware to produce the multiple inspection standards needed to establish common reject levels for each component inspected. Machining facsimile/duplicates of the inspected component from the same material is very expensive and does not truly represent the conditions encountered on the inspection surfaces of the service run hardware. Slight alterations to field engine components induced by engine operating extremes such as high temperature, wear, oxidation/sulfidation or, as is the case with most compressor disk blade slots, galling along the disk/blade contact surface, are often acceptable for continued operation, but greatly affect the eddy current scan baseline to the point of potential rejection of flight worthy hardware. These types of surface artifacts are not reproducible in a manufactured facsimile standard.

SUMMARY OF THE INVENTION

Accordingly, it is an object of the present invention to provide an eddy current sensitivity setting standard which can be easily applied and which is accurate.

The foregoing object is attained by the compliant laminar eddy current sensitivity standard.

In accordance with the present invention, a compliant laminar eddy current sensitivity standard is provided. The compliant laminar eddy current sensitivity standard comprises a sheet of nonconductive, nonmagnetic material, at least one strand of highly conductive material embedded in the nonconductive, nonmagnetic material, and an adhesive layer attached to a surface of the nonconductive, nonmagnetic material.

A method for using a compliant laminar eddy current sensitivity standard comprising the steps of providing a sheet of nonconductive, nonmagnetic material with at least one strand of highly conductive material embedded in the nonconductive, nonmagnetic material, and an adhesive layer attached to one surface of the nonconductive, nonmagnetic material; adhering said sensitivity standard on said surface of said part; and moving an eddy current probe over a surface of said sensitivity standard.

Other details of the compliant laminar eddy current sensitivity standard of the present invention, as well as other objects and advantages attendant thereto, will be set forth in the following detailed description and the accompanying drawings, wherein like reference numerals depict like elements.

DETAILED DESCRIPTION OF THE PREFERRED EMBODIMENT(S)

Figure 1:
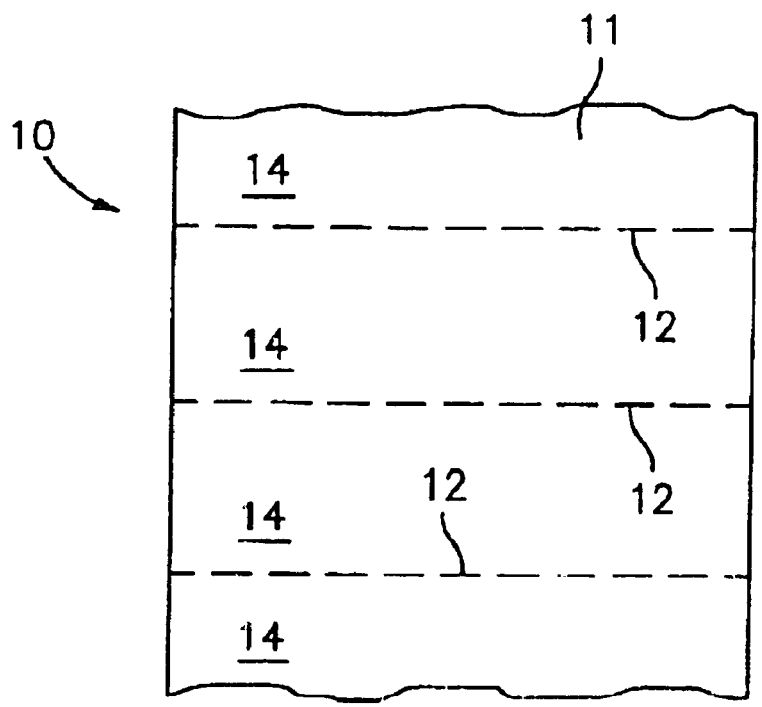
FIG. 1 is a top view of a compliant laminar eddy current sensitivity device in accordance with the present invention.
Figure 2:
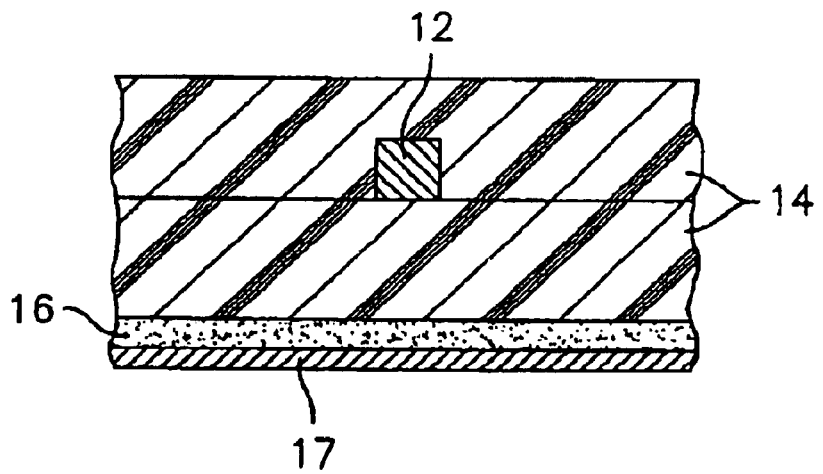
FIG. 2 is a side view of the compliant laminar eddy current sensitivity device of FIG. 1.

Referring now to the drawings, FIGS. 1 and 2 illustrate a compliant laminar eddy current sensitivity standard 10 in accordance with the present invention. The device 10 has particular utility for inspecting parts formed from low conductivity metals such as titanium based alloys and nickel based alloys.

The standard 10 comprises a sheet 11 having at least one thin strand 12 of highly conductive metal embedded in one or more layers of a nonconductive, nonmagnetic polymer material 14. In a preferred embodiment, the standard 10 comprises a sheet 11 having a plurality of highly conductive metal strands 12 spaced apart about 1.0 inch on center. While the sheet 11 forming the standard 10 may have any desired length and width, a typical sheet is about 16 inches by about 22 inches with 16 highly conductive metal strands 12. Individual sensitivity setting standards can be cut from the sheet 11 to a desired shape and size needed to fit a surface of a part to be inspected.

Each high conductive metal strand 12 may be formed from any suitable high conductivity material such as copper, copper alloys, aluminum, aluminum alloys, silver, silver alloys, gold, gold alloys, and mixtures thereof. For example, each strand 12 could be a copper wire having a diameter of about 0.0035 inches, a strip of aluminum foil having a width in the range of from about 0.050 inches to about 0.110 inches and a thickness in the range from about 0.002 inches to about 0.004 inches, or a strip of copper foil having a width in the range of from about 0.010 inches to about 0.040 inches and a thickness in the range of from about 0.0007 inches to about 0.0014 inches. The length of each strand 12 is the same as the overall length of the entire standard 10. When copper is used for the highly conductive metal strand 12, it should be present in an amount from about one-half ounce of copper per square foot to about 1.0 ounces of copper per square foot.

Each layer of polymer material 14 may be formed from a polyethylene terephthalate material, a polytetrafluoroethylene material, a polyamide material, or mixtures thereof. Preferably, each layer of polymer material 14 is in tape form. The layer(s) of polymer material 14 may have an overall thickness less than about 0.0060 inches, preferably less than about 0.0050 inches. A suitable polymer material 14 which may be used for the standard 10 is KAPTON.

The adhesive material 16 may comprise any suitable pressure sensitive adhesive known in the art, such as 3M Scotch VHB acrylic based pressure sensitive material. The thickness of the adhesive layer 16 may be as great as about 0.0015 inches, preferably less than or equal to about 0.0010 inches. A removable backing 17, such as a paper backing, may be applied to a surface of the adhesive material 16.

Figure 3:
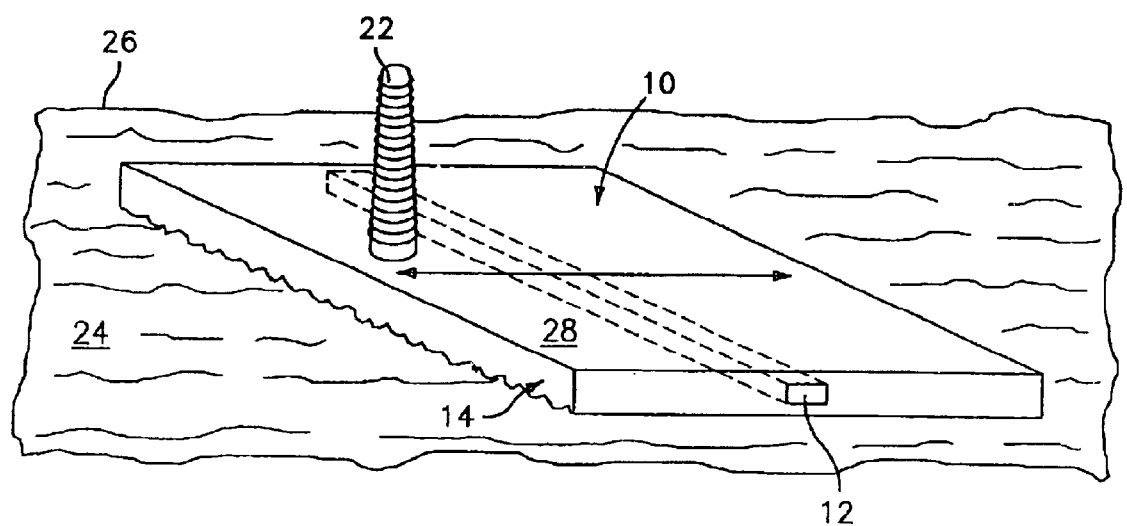
FIG. 3 is a perspective view of an individual sensitivity standard adhered to a surface of a part to be inspected and an eddy current probe being passed over a surface of the individual sensitivity standard.

During use, as shown in FIG. 3, an individual standard 10 may be cut from the sheet 11 into a desired shape and size and may be non-destructively placed on a surface 24 of a part 26 to be inspected after the backing 17 has been removed. Due to its thinness, the standard 10 conforms to the surface contours. An eddy current probe 22 is then passed over a surface 28 of the individual standard 10 to produce an instrument response during scan which is used to calibrate the eddy current system crack sensitivity. As the instrument response is not being produced by an actual crack, or by an EDM slot that closely simulates (physically) a crack, the responses produced by the proposed calibration system must be compared to and calibrated against actual cracks of known dimensions to establish response equivalencies. From the instrument response, the phase and amplitude can be adjusted to set the sensitivity of the inspection.

The standard 10 generates the perfect baseline during sensitivity setting albeit all geometric and electric surface effects are induced by the actual hardware. The response, produced as the eddy current probe 22 is passed over the high conductivity metal strand 12, performs accurate and consistent sensitivity setting for the eddy current system. As mentioned, this sensitivity setting is ultimately traceable to data taken on real cracks or EDM slots in a controlled master standard. The standard 10 traced back to a control master standard provides an inexpensive method to set the sensitivity of inspections performed at multiple field locations to the same level. After sensitivity is set, the standard 10 is removed from the part surface and stowed for future use or discarded.

One of the advantages to the design of the standard 10 derives from the fact that the sensitivity setting can be done with the component under test in the final inspection position. This becomes extremely important with the advent of robotic scanning systems. The sensitivity setting would be performed and recorded by scanning the inspected detail with the standard 10 in place at the critical area with the component fixtured in the final inspection position. The standard 10 would then be removed and the scanning system immediately activated to perform the calibrated inspection without probe disruption.

It is apparent that there has been provided in accordance with the present invention a compliant laminar eddy current sensitive standard which fully satisfies the objects, means, and advantages set forth hereinbefore. While the present invention has been described in the context of specific embodiments thereof, other alternatives, modifications, and variations will become apparent to those skilled in the art having read the foregoing description. Therefore, it is intended to embrace those alternatives, modifications, and variations as fall within the broad scope of the appended claims.

What is claimed is:

1. A compliant laminar eddy current sensitivity standard comprising:
   a sheet of nonconductive, nonmagnetic material having a first planar surface and a second surface;
   at least one strand of highly conductive material completely embedded in said sheet; and
   an adhesive layer affixed to said second surface of said nonconductive, nomnagnetic material, said adhesive layer contacting a part to be inspected.

2. A compliant laminar eddy current sensitivity standard according to claim 1, wherein said nonconductive, nomnagnetic material comprises a polymer material.

3. A compliant laminar eddy current sensitivity standard according to claim 2, wherein said polymer material is selected from the group consisting of a polyethylene terephthalate material, a polytetrafluoroethylene material, a polyamide material, and mixtures thereof.

4. A compliant laminar eddy current sensitivity standard according to claim 1, wherein said nonconductive, nonmagnetic material has a thickness less than about 0.0060 inches.

5. A compliant laminar eddy current sensitivity standard according to claim 1, wherein said nonconductive, nonmagnetic material has a thickness less than about 0.0050 inches.

6. A compliant laminar eddy current sensitivity standard according to claim 1, wherein said highly conductive material is selected from the group consisting of copper, copper alloys, aluminum, aluminum alloys, silver, silver alloys, gold, gold alloys, and mixtures thereof.

7. A compliant laminar eddy current sensitivity standard according to claim 6, wherein each said strand is formed from aluminum foil and has a width in the range of from about 0.050 inches to about 0.110 inches and a thickness in the range of from about 0.002 inches to about 0.004 inches.

8. A compliant laminar eddy current sensitivity standard according to claim 6, wherein each said strand is formed from a copper wire having a diameter of about 0.0035 inches.

9. A compliant laminar eddy current sensitivity standard according to claim 6, wherein each said strand is formed from a copper foil having a width in the range of about 0.010 inches to about 0.040 inches and a thickness in the range of from about 0.0007 inches to about 0.0014 inches.

10. A compliant laminar eddy current sensitivity standard according to claim 1, wherein said nonconductive, nonmagnetic material and each said highly conductive strand have the same length.

11. A compliant laminar eddy current sensitivity standard according to claim 1, wherein said adhesive layer is formed from a pressure sensitive adhesive.

12. A compliant laminar eddy current sensitivity standard according to claim 11, wherein said adhesive layer has a thickness as great as 0.0015 inches.

13. A compliant laminar eddy current sensitivity standard according to claim 11, wherein said adhesive layer has a thickness less than or equal to about 0.0010 inches.

14. A compliant laminar eddy current sensitivity standard according to claim 1, further comprising a removable backing material affixed to a surface of said adhesive layer.

15. A compliant laminar eddy current sensitivity standard according to claim 1, wherein said sheet has a size and shape which corresponds to the size and shape of a part to be inspected.

16. A method of using a compliant laminar eddy current sensitivity standard comprising the steps of:
   providing an individual sensitivity standard comprising a sheet of nonconductive, nonmagnetic material having a first exterior planar surface, at least one strand of highly conductive material embedded in the sheet and an adhesive layer affixed to a second surface of the nonconductive, nonmagnetic material;
   adhering said individual sensitivity standard to a surface of said part to be inspected; and
   passing an eddy current probe over said first exterior surface of said individual sensitivity standard.

17. A compliant laminar eddy current sensitivity standard comprising:
- a sheet of nonconductive, nonmagnetic material having a first planar surface and a second surface;
- at least one strand of highly conductive material completely embedded in said sheet;
- said at least one strand being narrower than said sheet; and
- an adhesive layer affixed to said second surface of said nonconductive, nonmagnetic material, said adhesive layer contacting a part to be inspected.

18. A compliant laminar eddy current sensitivity standard comprising:
- a sheet of nonconductive, nonmagnetic material having a first planar surface and a second surface;
- means for cooperating with an eddy current probe to calibrate eddy current system sensitivity;
- said cooperating means comprising at least one strand of a highly conductive material completely embedded in said sheet; and
- an adhesive layer affixed to said second surface of said nonconductive, nonmagnetic material, said adhesive layer contacting a part to be inspected.

* * * * *

UNITED STATES PATENT AND TRADEMARK OFFICE
CERTIFICATE OF CORRECTION

PATENT NO.        : 6,734,664 B2                                        Page 1 of 1
APPLICATION NO.   : 09/917979
DATED             : May 11, 2004
INVENTOR(S)       : David A. Bryson et al.

It is certified that error appears in the above-identified patent and that said Letters Patent is hereby corrected as shown below:

In column 4, claim 1, line 2, delete "nonmagnetic".
In column 4, claim 2, line 2, delete "nonmag-".
In column 4, claim 2, line 3, delete "netic".

Signed and Sealed this

Nineteenth Day of September, 2006

JON W. DUDAS
*Director of the United States Patent and Trademark Office*